United States Patent [19]

Powell et al.

[11] 4,418,064

[45] Nov. 29, 1983

[54] CHEMOTHERAPEUTICALLY ACTIVE MAYTANSINOIDS: TREFLORINE, TRENUDINE, AND N-METHYLTRENUDONE

[75] Inventors: Richard G. Powell, Peoria; Cecil R. Smith, Jr., Dunlap, both of Ill.

[73] Assignee: The United States of America as represented by the Secretary of Agriculture, Washington, D.C.

[21] Appl. No.: 426,439

[22] Filed: Sep. 29, 1982

[51] Int. Cl.³ ................ A61K 31/535; C07D 498/18
[52] U.S. Cl. .................. 424/248.54; 260/239.3 P
[58] Field of Search .................. 260/239.3 P; 424/248.54

[56] References Cited

U.S. PATENT DOCUMENTS 4,313,946  2/1982  Powell et al. .................. 424/248.54

OTHER PUBLICATIONS

B. Freedman et al., "Biological Activities of Trewia nudiflora Extracts Against Certain Economically Important Insect Pests," J. Chem. Ecol. 8(2): 409-418 (1982).

R. G. Powell et al., "Treflorine, Trenudine, and N-Methyltrenudone: Novel Maytansinoid Tumor Inhibitors Containing Two Fused Macrocyclic Rings," J. Amer. Chem. Soc. 104(18): 4929-4934 (Sep. 8, 1982).

"NCI Reviews Work on Natural Products," in Northern Regional Research Center Notes from the Director, Issue #1405 (Feb. 1, 1980).

"NCI Reviews Work on Natural Products," Northern Regional Research Center Notes from the Director (NRRC Notes), Issue #1405, Feb. 1, 1980.

R. G. Powell et al., "Novel Maytansinoid Tumor Inhibitors from Trewia nudiflora," Abstracts of Papers, Second Chemical Congress of the North American Continent, Aug. 24-29, 1980, Abstract No. 42.

R. G. Powell et al., "Novel Maytansinoid tumor Inhibitors from Trewia nudiflora: Trewiasine, Dehydrotrewiasine, and Demethyltrewiasine," J. Org. Chem. 46: 4398-4403 (Oct. 23, 1981).

R. G. Powell et al., "Treflorine, Trenudine, and N-Methyltrenudone: Novel Maytansinoid Tumor Inhibitors Containing Two Fused Macrocyclic Rings," American Chemical Society, 16th Great Lakes Regional Meeting, Jun. 7-9, 1982, Abstract No. 56.

Chemical Abstracts, vol. 97, Item 107040t (1982) Abstracting Powell et al. in "J. Am. Chem. Soc." (1982), vol. 104, No. 18, pp. 4929-4934.

Chemical Abstracts vol. 96, Item 212490s (1982), Abstracting Freedman et al. in "J. Chem. Ecol." 1982) vol. 8, No. 2, pp. 409-418, (Including Corresponding Chemical Substances Index Reference).

Primary Examiner—Robert T. Bond
Attorney, Agent, or Firm—M. Howard Silverstein; David G. McConnell; Curtis P. Ribando

[57] ABSTRACT

A novel group of maytansinoid compounds has been discovered in the seed tissue of *Trewia nudiflora*. They are represented by the general formula

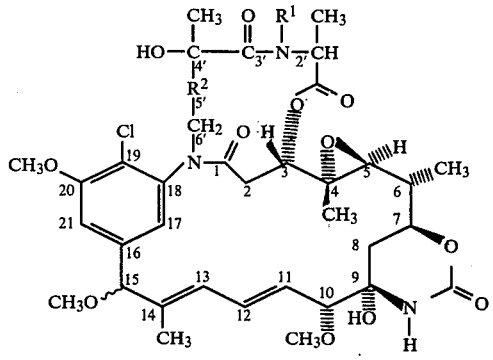

and are uniquely characterized by a 12-membered ring joining C-3 and the amide nitrogen at C-18, and also by a distinguishing methoxy group on the C-15 carbon. These isolates have proven to be effective in causing the remission of one or more types of malignancies.

8 Claims, No Drawings

CHEMOTHERAPEUTICALLY ACTIVE MAYTANSINOIDS: TREFLORINE, TRENUDINE, AND N-METHYLTRENUDONE

BACKGROUND OF THE INVENTION

1. Field of the Invention

This invention relates to a novel group of ansa macrolide compounds which have utility, inter alia, as chemotherapeutic agents for the remission of malignancies in animals.

2. Description of the Prior Art

The isolation of three ansa macrolides from ethanolic extracts of *Maytenus ovatus* and *Maytenus buchanii* was first reported by S. M. Kupchan et al. and is the subject of U.S. Pat. No. 3,896,111. These maytanside esters are characterized by the structural formula

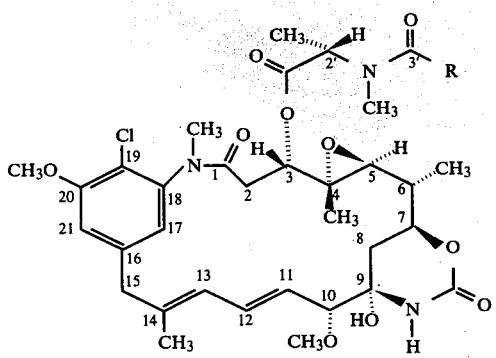

and include maytansine in which R=CH$_3$, maytanprine in which R=CH$_2$CH$_3$, and maytanbutine in which R=CH(CH$_3$)$_2$. Kupchan reports that these compounds showed activity against lymphocytic leukemia P388 when administered at a level in the range of 20 to 100 micrograms/kg. of body weight. Two analogs of maytanbutine isolated from *Colubrina texensis* are taught by Wani et al. [J.C.S. Chem. Commun. page 390 (1973)] in which the C-15 position bears either an hydroxyl (colubrinol) or an acetate (colubrinol acetate) side chain. These compounds have also demonstrated activity against lymphocytic leukemia P388 at the microgram per kilogram level, and in addition show cytotoxicity (ED$_{50}$) against KB cell culture at $10^{-4}$–$10^{-5}$ μg./ml. In a later publication by Kupchan et al. [J. Org. Chem. 42: 2349–57 (1977)] a variety of maytansinoids are reviewed and are categorized as either maytanside esters (those having a C-3 ester side chain) or as maytansides (those lacking the C-3 ester side chain). Of particular significance is the disclosure of finding yet another antileukemic principle, maytanbutacine. This maytanside ester was isolated from *Maytenus serrata* and is similar to colubrinol acetate in that it has an acetate side chain in the C-15 position. The difference lies in the C-3 ester group, which is

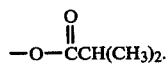

This reference also teaches the isolation of maytansine and related compounds from another celastraceous plant, *Putterlickia verrucosa*.

The significance ascribed to the various structural entities of the maytansinoids for antileukemic activity is discussed by Kupchan et al. [J. Med. Chem. 21: 31–37 (1978)]. Most important for activity is the presence of a C-3 ester, and the particular structure of the ester is also an influencing factor. The C-9 carbinolamide moiety is shown to be critical for optimal activity. In Table II of this publication, the ED$_{50}$ level against KB cell culture of the previously mentioned maytansinoids is shown to be in the range of $10^{-5}$–$10^{-7}$ μg./kg.

Higashide et al. [Nature 270: 721–722 (1977) and U.S. Pat. No. 4,225,494] and Asai et al. [Tetrahedron 35: 1079–85 (1979)] first reported the isolation of ansamitocins, a group of ansamycin antibiotics, from a fermentation broth of *Nocardia* sp. No. C-15003 (N-1). The structures of these compounds are similar to maytansine, differing only with respect to the C-3 moiety. Ansamitocin demonstrated strong growth inhibitory activities against certain phytopathogenic fungi, dermatophytes, and certain protozoa. Two of the compounds also possess antitumor activity against the P388 strain at doses as low as 0.8–25 μg./kg. body weight, as well as significant activity against B16 melanoma, sarcoma 180, Ehrlich carcinoma, and P815 mastocytoma. Some activity was also shown against leukemia L1210.

In U.S. Pat. No. 4,313,946, Powell et al. disclosed the isolation from *Trewia nudiflora* L. of a class of maytansinoids characterized by a methoxy group on the C-15 carbon. The compounds included trewiasine, dehydrotrewiasine, and 3'-N-demethyltrewiasine, with at least the former two demonstrating activity in the PS system at 4 μg./kg. dosage level. Also, trewiasine was shown by Freedman et al. (U.S. Pat. No. 4,315,929) as being effective in controlling the European corn borer.

SUMMARY OF THE INVENTION

We have now unexpectedly discovered another class of ansa macrolides in the plant tissue of *Trewia nudiflora* L. which not only are characterized by a C-15 methoxy substituent but also uniquely contain two fused macrocyclic rings. That is, in addition to the 19-membered ring characteristic of all previously known maytansinoids, these new compounds have a 12-membered ring joining C-3 and the amide nitrogen at C-18. Hence, this group of compounds is represented by the structural formula

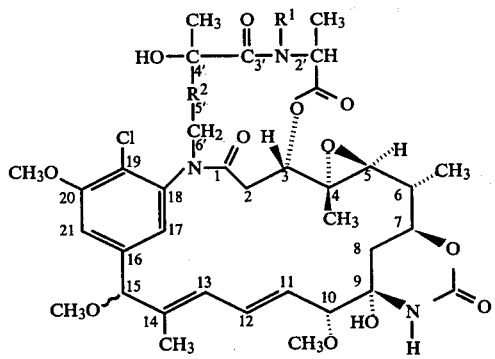

and includes:
treflorine: R$^1$=—H and R$^2$=—CH$_2$—;
trenudine: R$^1$=—H and R$^2$=—CHOH—; and
N-methyltrenudone: R$^1$=—CH$_3$ and R$^2$=

All three of the above-mentioned maytanside esters are active in at least one experimental tumor system and exhibit cytotoxicity at a level of one or more orders of magnitude less than that reported by Kupchan for compounds such as maytansine and maytanbutine.

In accordance with this discovery, it is an object of the invention to provide a novel group of ansa macrolides having utility as chemotherapeutic agents.

It is also an object of the invention to isolate these compounds from the tissue of *Trewia nudiflora*.

A further object of the invention is to prepare chemotherapeutic compositions active against a variety of cancerous disorders.

Another object of the invention is to prepare chemotherapeutic compositions having relatively low cytotoxicity toward the subject organism.

Other objects and advantages of this invention will become readily apparent from the ensuing description.

DETAILED DESCRIPTION OF THE INVENTION

The starting material for use in the invention is the seed of *Trewia nudiflora* L. (Euphorbiaceae), and it is considered likely that other tissues of the plant would also contain extractable quantities of the subject compounds.

The seed material is prepared for extraction by grinding it in a conventional mill to a suitable particle size, usually in the range of about 0.001-3 mm. in diameter, and more preferably in the range of 0.1-2 mm. The ground material is defatted by extraction with a nonpolar solvent such as hexane, followed by extraction with 95% ethanol or similar polar solvent. The extract is separated from the solid residue and then subjected to a solvent partitioning scheme as described in detail, below, toward the end of obtaining a crude maytansinoid-containing extract.

Separation and purification of the instant maytanside esters from the crude extract can be effected by the use of the proper combination of conventional techniques including, for example, column chromatography (CC), thin-layer chromatography (TLC), and high-pressure liquid chromatography (HPLC). While not desiring to be limited thereto, the details of the separation procedure are illustrated by the following example. Fractionation of the ethanolic extract was guided by assay against KB cell culture and PS leukemia in mice.

EXAMPLE

Isolation of Compounds

Extraction Procedures

*Trewia nudiflora* seed (114 kg.) was ground in a Wiley mill to a particle size of less than about 2 mm. in diameter. The ground material was divided into 16 batches, and defatted with hexane in a pilot-plant scale Soxhlet extractor yielding 21 kg. of oil. Each batch was then further extracted with 95% ethanol, yielding a combined total of 7.25 kg. of ethanol soluble material. Ethanol solubles were divided into six equal portions, and each portion was partitioned between 6 l. of ethyl acetate and 6 l. of water; aqueous phases were then backwashed two times with 3-l. portions of ethyl acetate. Combined ethyl acetate extracts were evaporated, and the resulting thick syrup was partitioned between 13 l. of hexane and 13 l. of 10% aqueous methanol; the hexane layer was backwashed with 6.5 l. additional aqueous methanol. The combined aqueous methanol soluble material was evaporated to a thick syrup and partitioned between 13 l. each of $CHCl_3$ and $H_2O$. The aqueous layer was then backwashed twice with 6.5-l. portions of $CHCl_3$ and the combined $CHCl_3$ extracts were evaporated to dryness, yielding 710 g. of highly cytotoxic material.

Chromatographic Separations

The $CHCl_3$ soluble fraction, 710 g., was divided into 13 portions, and each was subjected to column chromatography on a 6-cm. ID column packed with 300 g. of silica per run. Elution was carried out by successive application of 1.5 l. each of the following solvents: $CHCl_3$, $CHCl_3$—MeOH (19:1), $CHCl_3$—MeOH (3:2), and MeOH. Similar fractions were combined on the basis of TLC analysis and the most active material (167 g.), as determined by bioassay was collected near the middle of each run or during elution with $CHCl_3$—MeOH (9:1). Further chromatography of this material was carried out in six portions on a 6-cm. ID column, 280 g. of silica per run, using 1.5 l. of each of the following solvents: hexane-ethyl acetate (1:4), ethyl acetate, ethyl acetate-MeOH (19:1), ethyl acetate-MeOH (9:1), ethyl acetate-MeOH (1:1). Similar fractions were again combined on the basis of TLC analysis and 17 g. of highly cytotoxic material was selected for further study. The concentrate was split into four portions and each was then chromatographed on a reversed phase column. Each sample was deposited on approximately 90 cm.³ of $C_{18}$ silica packed in a precolumn, which was placed in a preparative HPLC instrument ahead of a $C_{18}$ cartridge. Columns were then eluted with 3.5 l. of MeOH-$H_2O$ (7:3) and the complex of Trewia maytansinoids emerged as a broad peak at column volumes of 1.5-3.5. Samples were arbitrarily collected across the peak yielding 12 fractions and a total of 8.4 g. of material, mainly mixtures of trewiasine, dehydrotrewiasine, demethyltrewiasine, treflorine, trenudine, and N-methyltrenudone. Individual compounds were obtained by semi-preparative HPLC on a $C_{18}$ μ-Bondapak column in 15-mg. portions eluting with MeOH—$H_2O$ (65:35) and operating at 2 ml. per minute; each fraction was further purified by preparative TLC and recrystallized from $CH_2Cl_2$-hexane. Elution times and yields obtained under these conditions were reported in Table I, below.

CHARACTERIZATION OF COMPOUND STRUCTURES

The structures of the isolated fused-ring compounds of this invention are determined primarily by high resolution mass spectrometry and by proton and carbon-13 NMR using trewiasine as the standard for comparison. Characterization of the recrystallized compounds is as follows:

Treflorine. M.p. 205°-208° C. (d); IR ($CHCl_3$) 3600, 3440, 1760, 1715, 1675, 1640, 1610, 1590 cm.$^{-1}$; UV$_{max}$ (EtOH) 233 nm. ($\epsilon$ 24,000), 243 (sh, 18,500), 253 (19,850), 282 (5,060), 288 (5,060); $[\alpha]_D^{23}$ −138° (c 0.045, $CHCl_3$); mass spectrum (70 eV) m/z (relative intensity) 688 (M+—a, 2.7), 188 (5.7), 149 (4.2), 69 (14.7), 58 (32.1), 55 (13.4), 44 (100). Found: M+—($H_2O$+H-NCO), 688.2751; $C_{35}H_{45}ClN_2O_{10}$ requires 688.2762.

Trenudine. M.p. 200°–205° C. (d); IR (CHCl$_3$) 3600, 3450, 3360, 1760, 1715, 1665, 1610, 1590 cm.$^{-1}$; UV$_{max}$ (EtOH) 233 nm. ($\epsilon$ 26,400), 248 (sh, 21,500), 253 (22,600), 282 (6,130), 288 (6,130); [$\alpha$]$_D^{23}$ −114° (c 0.24, CHCl$_3$); mass spectrum (70 eV) m/z (relative intensity) 704 (M$^+$—a, 3.9) 672 (2.4), 669 (2.6), 593 (2.6), 204 (3.2), 185 (3.1), 171 (5.5), 95 (10.2), 85 (10.5), 83 (11.7), 81 (11.5), 69 (16.9), 55 (23.9), 44 (100). Found: M$^+$—(H$_2$O+HNCO), 704.2711; C$_{35}$H$_{45}$ClN$_2$O$_{11}$ requires 704.2711.

TABLE I

| Compound | Elution time (min.) | Yield mg. | % by Weight |
|---|---|---|---|
| trewiasine | 33.0 | 3700 | 3.2 × 10$^{-3}$ |
| dehydrotrewiasine | 27.5 | 191 | 1.6 × 10$^{-4}$ |
| demethyltrewiasine | 31.0 | 25 | 2.0 × 10$^{-5}$ |
| treflorine | 25.5 | 207 | 1.8 × 10$^{-4}$ |
| trenudine | 12.5 | 743 | 6.5 × 10$^{-4}$ |
| N—methyltrenudone | 15.0 | 127 | 1.1 × 10$^{-4}$ |

N-Methyltrenudone. M.p. 192°–197° C. (d); IR (CHCl$_3$) 3600, 3450, 1760, 1720, 1675, 1640, 1590 cm.$^{-1}$; UV$_{max}$ (EtOH) 233 nm. ($\epsilon$ 27,000), 247 (sh, 21,300), 252 (21,900), 282 (5,270), 289 (5,470); [$\alpha$]$_D^{23}$ −110° (c 0.183, CHCl$_3$); mass spectrum (70 eV) m/z (relative intensity) 716 (M$^+$—a, 12.3), 681 (4.4), 605 (2.6), 542 (7.5), 292 (10.0), 109 (15.1), 75 (47.7), 71 (18.3), 58 (100), 55 (27.7), 44 (74.6), 43 (48.1). Found M$^+$—(H$_2$O+HNCO), 716.2662; C$_{36}$H$_{45}$ClN$_2$O$_{11}$ requires 716.2711.

The $^1$H and $^{13}$C NMR values of these compounds as compared to trewiasine are reported in Tables II and III, below.

CHEMOTHERAPEUTIC ACTIVITY

It is noteworthy that biological activity in the maytansinoid series is fully retained in compounds with the additional macrocyclic rings linking C-3 and the aromatic amide nitrogen. The KB Cell Culture Screen used in guiding the above-described fractionations was conducted in accordance with the National Cancer Institute (NCI) Protocol 1.600 [Geran et al., Cancer Chemother. Rep., Part 3, 3: 17 (1972)] in which the effectiveness of the test compounds against cultivated cells of human epidermoid carcinoma of the mouth was evaluated. The results of this procedure are expressed as the dose that inhibits growth to 50% of control growth by 3 days after drug addition. Such a dose is referred to as ED$_{50}$ and activity is indicated for ED$_{50}$ levels of $\leq$30 μg./ml. The smaller the ED$_{50}$ level, the more cytotoxic the test material. The activities of the crystallized compounds isolated above are reported below in Table IV.

TABLE IV

| KB Activities for Isolated Compounds | |
|---|---|
| Compound | ED$_{50}$ (μg./ml.) |
| trewiasine | 2.0 × 10$^{-4}$ |
| treflorine | 2.7 × 10$^{-4}$ |
| trenudine | 6.4 × 10$^{-4}$ |
| N—methyltrenudone | <1.0 × 10$^{-2}$ |

TABLE II $^1$H NMR Spectral Data[1]

| Proton assignment | Trewiasine | Treflorine | Trenudine | N—Methyltrenudone |
|---|---|---|---|---|
| 2$_A$ | 2.18 dd | 2.21 dd | 2.22 dd | 2.09 dd |
|  | J=14.3,3.0 | J=14.9,3.9 | J=13.6,3.7 | J=14.7,3.6 |
| 2$_B$ | 2.55 dd | 2.50 dd | 2.53 dd | 2.62 dd |
|  | J=14.3,12.2 | J=14.9,12.0 | J=13.6,12.0 | J=14.7,12.0 |
| 3 | 4.75 dd | 4.51 dd | 4.63 dd | 4.51 dd |
|  | J=12.2,3.0 | J=12.0,3.9 | J=12.0,3.7 | J=12.0,3.6 |
| 4 CH$_3$ | 0.76 s | 0.72 s | 0.80 s | 0.82 s |
| 5 | 3.01 d | 3.07 d | 2.98 d | 3.06 d |
|  | J=9.6 | J=9.8 | J=9.8 | J=9.8 |
| 6 CH$_3$ | 1.27 d | 1.29 d | 1.30 d | 1.29 d |
|  | J=6.2 | J=6.4 | J=6.4 | J=5.3 |
| 7 | 4.28 m | 4.22 m | 4.21 m | 4.18 m |
| 10 | 3.51 d | 3.52 d | 3.55 d | 3.54 d |
|  | J=9.1 | J=9.0 | J=8.8 | J=8.8 |
| 11 | 5.72 dd | 5.59 dd | 5.68 dd | 5.68 dd |
|  | J=15.3,9.1 | J=15.2,9.0 | J=15.4,8.8 | J=15.4,8.8 |
| 12 | 6.46 dd | 6.48 dd | 6.52 dd | 6.52 dd |
|  | J=15.3,11.1 | J=15.2,10.9 | J=15.4,10.8 | J=15.4,10.7 |
| 13 | 6.98 d | 6.60 d | 6.72 d | 6.67 d |
|  | J=11.1 | J=10.9 | J=10.8 | J=10.7 |
| 14 CH$_3$ | 1.52 s | 1.57 s | 1.55 s | 1.53 s |
| 15 | 4.86 s | 4.95 s | 4.88 s | 4.87 s |
| 17 | 6.54 d | 7.26 d | 7.26 d | 7.25 d |
|  | J=1.5 | J=1.6 | J=1.6 | J=1.5 |
| 21 | 7.22 d | 7.47 d | 7.27 d | 7.54 d |
|  | J=1.5 | J=1.6 | J=1.6 | J=1.5 |
| 10 OCH$_3$[2] | 3.35 s | 3.39 s | 3.42 s | 3.40 s |
| 15 OCH$_3$[2] | 3.37 s | 3.41 s | 3.43 s | 3.42 s |
| 20 OCH$_3$ | 3.99 s | 4.02 s | 4.00 s | 3.99 s |
| 18 NCH$_3$ | 3.16 s | — | — | — |
| 2' | 5.37 m | 4.79 m | 4.95 m | 5.57 q |
| 2' CH$_3$ | 1.28 d | 1.33 d | 1.34 d | 1.29 d |
|  | J=6.8 | J=6.9 | J=7.0 | J=7.0 |
| 2' NCH$_3$ | 2.88 s | — | — | 2.75 s |
| 4' | 2.76 m | — | — | — |
| 4' CH$_3$ | 1.06 d | 1.40 s | 1.48 s | 1.53 s |
|  | 1.12 d | | | |
| 5'$_A$ | — | 1.45 m | 3.93 m | — |
|  |  | J=14.2,3.0 | J=2.5,2.4 |  |

TABLE II-continued

$^1$H NMR Spectral Data[1]

| Proton assignment | Trewiasine | Treflorine | Trenudine | N—Methyltrenudone |
|---|---|---|---|---|
| 5'$_B$ | — | 2.78 m<br>J=14.2,3.0 | — | — |
| 6'$_A$ | — | 3.03 m<br>J=14.2,3.0 | 3.55 dd<br>J=15.0 | 4.17 d<br>J=14.6 |
| 6'$_B$ | — | 4.46 m<br>J=14.2,3.0 | 4.49 dd<br>J=15.0 | 4.51 d<br>J=14.6 |
| 9 NH | 6.23 s | 6.22 s | 6.25 s | 6.20 s |
| 2' NH | — | 7.06 d<br>J=10.7 | 7.67 d<br>J=9.9 | — |

[1]Chemical shifts (δ) are expressed in p.p.m. from internal tetramethylsilane, and coupling constants (J) are expressed in Hz. Extensive decoupling was used to verify assignments. Spectra were recorded in deuteriochloroform solution on a Nicolet NT-470 spectrometer. In all of the above, the C-6 and C-8 proton signals occur at approximately δ1.3 and are obscured by other signals in this region.
[2]These assignments may be reversed.

TABLE III

$^{13}$C NMR Spectral Data[1]

| Carbon assignments | Trewiasine | Treflorine | Trenudine | N—Methyltrenudone |
|---|---|---|---|---|
| 2 | 32.4 t | 32.5 t | 33.1 t | 32.4 t |
| 3 | 78.2 d | 78.5 d | 78.5 d | 78.8 d |
| 4 | 60.0 s | 59.4 s | 59.5 s | 59.5 s |
| 5 | 67.7 d | 67.1 d | 66.9 d | 66.7 d |
| 6 | 38.9 d | 37.8 d | 37.9 d | 38.1 d |
| 7 | 74.1 d | 74.0 d | 74.0 d | 71.4 d |
| 8 | 36.3 t | 36.1 t | 36.2 t | 36.2 t |
| 9 | 80.7 s | 80.8 s | 80.8 s | 81.0 s |
| 10 | 85.5 d | 88.7 d | 88.6 d | 88.6 d |
| 11 | 129.9 d | 128.9 d | 129.3 d | 129.3 d |
| 12 | 132.5 d | 132.6 d | 132.4 d | 132.6 d |
| 13 | 128.0 d | 126.5 d | 127.2 d | 127.3 d |
| 14 | 142.1 s | 141.9 s | 141.9 s | 141.7 s |
| 15 | 86.7 d | 87.0 d | 86.6 d | 86.9 d |
| 16 | 141.3 s | 140.7 s | 141.5 s | 141.4 s |
| 17 | 120.3 d | 121.9 d | 120.7 d | 120.7 d |
| 18 | 139.0 s | 139.1 s | 140.3 s | 140.4 s |
| 19 | 118.9 s | 118.2 s | 118.2 s | 118.7 s |
| 20 | 156.3 s | 156.2 s | 156.0 s | 156.3 s |
| 21 | 109.0 d | 109.0 d | 109.0 d | 108.6 d |
| C=O | 176.7 s | 176.1 s | 175.0 s | 171.4 s |
| C=O | 170.9 s | 171.8 s | 174.9 s | 171.1 s |
| C=O | 168.8 s | 170.9 s | 170.8 s | 169.5 s |
| C=O | 152.4 s | 152.5 s | 152.6 s | 152.5 s |
| OCH$_3$ | 56.3–7<br>3 q | 56.3–8<br>3 q | 56.4–9<br>3 q | 56.7–9<br>3 q |
| CH$_3$ | 14.6 q | 15.7 q | 16.2 q | 14.4 q |
| CH$_3$ | 13.1 q | 14.3 q | 14.2 q | 12.9 q |
| CH$_3$ | 12.0 q | 12.1 q | 12.0 q | 12.3 q |
| CH$_3$ | 10.0 q | 9.8 q | 9.9 q | 10.1 q |
| 18 NCH$_3$ | 35.2 q | — | — | — |
| 2' NCH$_3$ | 30.4 q | — | — | 30.2 q |
| 2' | 52.4 d | 46.3 d | 46.7 d | 52.6 d |
| 4' | 30.4 d | 73.4 s | 72.2 s | 78.5 s |
| 4' CH$_3$ | 19.4 q<br>18.8 q | 28.9 q | 28.5 q | 23.6 q |
| 5' | — | 35.6 t | 79.1 d | 204.0 s |
| 6' | — | 43.8 t | 52.4 t | 57.8 t |

[1]Chemical shifts (δ) are expressed in p.p.m. from internal tetramethylsilane. Proton decoupled and off-resonance decoupled spectra were recorded in deuteriochloroform solution on a Fourier transform Bruker WH-90 spectrometer.

Another indication of fraction activity is the effectiveness in the PS system against lymphocytic leukemia P388 in mice. These assays are conducted according to the NCI Protocol 1.200 described in Geran et al., supra. Starting 24 hours after the tumor implantation, previously determined doses of each compound were injected intraperitoneally once a day for 9 days. Survival time of treated leukemic mice is compared to that of untreated mice (T/C×100). A T/C value of 100% indicates no activity. A T/C value greater than 100% means that the treated mice are surviving longer than the control mice. A compound giving a T/C value greater than 125% is indicative of activity as defined by the NCI Protocols, above. The results for the isolated compounds are reported below in Table V.

The compounds were also evaluated in the B1 system against B16 melanocarcinoma in mice. This assay is conducted in accordance with the NCI Protocol 1.300 described in Geran et al., supra. Starting 24 hours after the tumor implantation, predetermined doses of the compound were injected intraperitoneally once a day for 9 days. The results are reported in Table VI below as the percent T/C.

The expressions "effective amount," "effective dose," and the like as referring to the treatment of animals are defined herein to mean those quantities of maytanside esters which will promote remission of the cancerous growth in the animal to which it is administered, without imparting a toxic response. The effective amount may vary with the injection vehicle, the injection schedule, the sex and species of host, the strain of tumor, and other related factors, all of which may be varied without departing from the scope or operativeness of the invention. In the PS and B1 systems tested, doses on the order of 1–32 μg./kg. body weight/day were generally found to be effective. These levels compare favorably with the activity observed for other maytansinoids, including the ansamitocins.

TABLE V

PS Activity for Isolated Compounds

| Compound | Vehicle[1] | Host sex | Dose (μg./kg./inj.)[2] | T/C (%) |
|---|---|---|---|---|
| trewiasine | M | F | 64.00 | 91 |
| | | | 32.00 | 128 |
| | | | 16.00 | 154 |
| | | | 8.00 | 140 |
| | | | 4.00 | 163 |
| treflorine | * | M | 32.00 | 150 |
| | | | 16.00 | 157 |
| | | | 8.00 | 144 |
| | | | 4.00 | 150 |
| trenudine | * | F | 32.00 | toxic |
| | | | 16.00 | 137 |
| | | | 8.00 | 146 |
| | | | 4.00 | 137 |
| | | | 2.00 | 144 |
| N—methyl-trenudone | * | M | 32.00 | toxic |
| | | | 16.00 | toxic |
| | | | 8.00 | 108 |
| | | | 4.00 | 153 |

[1]M = "Klucel" (hydroxypropylcellulose);
* = distilled water + alcohol.
[2]The doses are reported as micrograms per kilogram of host body weight per injection.

TABLE VI

B1 Activity for Isolated Compounds

| Compound | Vehicle[1] | Host sex | Dose (μg./kg./inj.)[2] | T/C (%) |
|---|---|---|---|---|
| trewiasine | M | M | 32.00 | 183 |
| | | | 16.00 | 172 |
| | | | 8.00 | 185 |
| | | | 4.00 | 157 |
| | | | 2.00 | 140 |
| | | | 1.00 | 133 |
| treflorine | * | M | 32.00 | 178 |
| | | | 16.00 | 162 |
| | | | 8.00 | 160 |
| | | | 4.00 | 130 |
| trenudine | * | M | 32.00 | toxic |
| | | | 16.00 | 197 |
| | | | 8.00 | 176 |
| | | | 4.00 | 145 |
| | | | 2.00 | 147 |
| | | | 1.00 | 137 |
| N—methyl-trenudone | * | M | 32.00 | 95 |
| | | | 16.00 | 111 |
| | | | 8.00 | 93 |

TABLE VI-continued

B1 Activity for Isolated Compounds

| Compound | Vehicle[1] | Host sex | Dose (μg./kg./inj.)[2] | T/C (%) |
|---|---|---|---|---|
| | | | 4.00 | 109 |

[1]M = "Klucel" (hydroxypropylcellulose);
* = distilled water + alcohol.
[2]The doses are reported as micrograms per kilogram of host body weight per injection.

Activities of at least treflorine and trenudine in the KB system are shown to be at least one order of magnitude less than that reported by Kupchan (J. Med. Chem. 21, Table II) for compounds such as maytansine, maytanbutine, maytanprine, and maytanbutacine. For this reason, these isolates show potential for displaying fewer side effects in in vivo treatments. Any pharmaceutically acceptable vehicle or carrier may be used in conjunction with the instant compounds.

It is understood that the foregoing detailed description is given merely by way of illustration and that modification and variations may be made therein without departing from the spirit and scope of the invention.

We claim:

1. A substantially pure compound selected from the group consisting of treflorine, trenudine, and N-methyltrenudone characterized by the formula

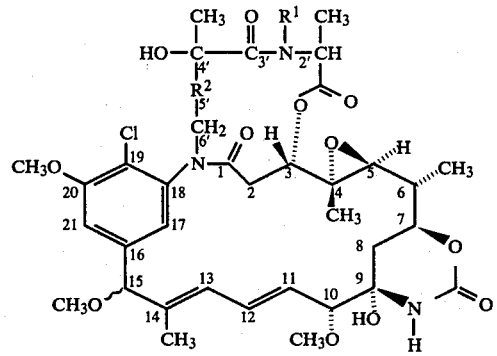

wherein for treflorine: $R^1 =$ —H and $R^2 =$ —CH$_2$—;
wherein for trenudine: $R^1 =$ —H and $R^2 =$ —CHOH—; and
wherein for N-methyltrenudone: $R^1 =$ —CH$_3$ and $R^2 =$

2. The substantially pure compound treflorine as described in claim 1.

3. The substantially pure compound trenudine as described in claim 1.

4. The substantially pure compound N-methyltrenudone as described in claim 1.

5. A chemotherapeutic composition suitable for the remission of leukemia comprising a pharmaceutically acceptable vehicle and an amount effective to promote said remission of a substantially pure compound selected from the group consisting of treflorine, trenudine, and N-methyltrenudone.

6. A composition as described in claim 5 wherein said compound is treflorine.

7. A composition as described in claim 5 wherein said compound is trenudine.

8. A composition as described in claim 5 wherein said compound is N-methyltrenudone.

* * * * *